US012757846B2

(12) United States Patent
Gaudino

(10) Patent No.: US 12,757,846 B2
(45) Date of Patent: Oct. 13, 2026

(54) *CANNABIS* PLANT NAMED 'LPA004'

(71) Applicant: FRONT RANGE BIOSCIENCES, INC., Boulder, CO (US)

(72) Inventor: Reginald Gaudino, Boulder, CO (US)

(73) Assignee: FRONT RANGE BIOSCIENCES, INC., Boulder, CO (US)

( * ) Notice: Subject to any disclaimer, the term of this patent is extended or adjusted under 35 U.S.C. 154(b) by 717 days.

(21) Appl. No.: 17/651,327

(22) Filed: Feb. 16, 2022

(65) Prior Publication Data

US 2022/0256799 A1 Aug. 18, 2022

Related U.S. Application Data

(60) Provisional application No. 63/150,401, filed on Feb. 17, 2021.

(51) Int. Cl.

*A01H 6/28* (2018.01)
*A01H 5/02* (2018.01)
*A01H 5/10* (2018.01)
*A01H 5/12* (2018.01)

(52) U.S. Cl.

CPC ................. *A01H 6/28* (2018.05); *A01H 5/02* (2013.01); *A01H 5/10* (2013.01); *A01H 5/12* (2013.01)

(58) Field of Classification Search

None

See application file for complete search history.

(56) References Cited

U.S. PATENT DOCUMENTS

PP30,668 P3 * 7/2019 Holmes ................ A61K 36/185 Plt./263.1

* cited by examiner

*Primary Examiner* — Vinod Kumar

(74) *Attorney, Agent, or Firm* — HUNT IP LAW

(57) ABSTRACT

The unique annual herbaceous *Cannabis* plant variety 'LPA004' is provided.

6 Claims, 6 Drawing Sheets
(6 of 6 Drawing Sheet(s) Filed in Color)

*CANNABIS* PLANT NAMED 'LPA004'

CROSS REFERENCE TO RELATED APPLICATIONS

The present Application for Patent claims priority to Provisional Application No. 63/150,401 entitled "*CANNABIS* PLANT NAMED 'LPA004'" filed Feb. 17, 2021, which is hereby expressly incorporated by reference herein.

LATIN NAME OF THE GENUS AND SPECIES

Genus—*Cannabis.*
Species—*sativa.*

VARIETY DENOMINATION

The new *Cannabis* plant claimed is of the variety denominated 'LPA004'.

BACKGROUND OF THE INVENTION

Field of the Invention

The present invention relates to a new and distinct annual variety of *C. sativa*, which has been given the variety denomination of 'LPA004'. 'LPA004' is intended for use as a medicinal herb for sale in *Cannabis* dispensaries.

Background of the Related Art

The genus *Cannabis* has been in use by humans for millennia, due to the multiplicity of its benefits, including the considerable value and utility of its fiber, the nutritional value of its seeds, and the medicinal value of its floral parts and products made from them. Currently, the genus is under intense legal commercialization in the United States as industrial hemp for a variety of purposes, including biodegradable plastics and building materials, clothing, paper, food, fuel, and medicines.

Cannabidiol (CBD) extracted from *Cannabis* is widely used in over-the-counter medicines and topical treatments and is also the active ingredient in the FDA-approved drug Epidiolex®. CBD is just one of at least dozens—perhaps hundreds—of cannabinoids endogenous to *Cannabis*, tetrahydrocannabinol (THC) being the other cannabinoid that is most well-known. The cannabinoids interact as a group with the human endocannabinoid receptors, which are distributed in the brain and throughout the body. The study of the endocannabinoid system (ECS) in humans and other mammals is an area of increasing interest and holds tremendous promise for the future of medicine. See, e.g., Russo (2019). *Cannabis* and Pain, *Pain Medicine,* 20(10): 1093/pm/pnz227; and Russo (2016). Clinical Endocannabinoid Deficiency Reconsidered: Current Research Supports the Theory in Migraine, Fibromyalgia, Irritable Bowel, and Other Treatment-Resistant Syndromes, *Cannabis Cannabinoid Res.* 1(1): 154-165.

Non-hemp forms of *Cannabis*, frequently referred to as marijuana, have been legalized for medicinal use in many states and also for adult use in a growing number of states. It is expected that the wave of legalization will continue to the point of some form of federal legalization or decriminalization.

Typically, marijuana products are available to users for purchase in specialized "dispensaries" that offer dried flower, edibles, tinctures, extracts, and the like. In some cases, a unique or unusual chemical profile, or chemotype, is attractive not only for flower sales but also for use in the preparation of extracts and/or isolates and for the manufacture of a variety of products that possess characteristics of the chemotype.

SUMMARY OF THE INVENTION

The present invention relates to a new and distinct annual variety of *C. sativa*, which has been given the variety denomination of 'LPA004'. 'LPA004' is intended for use as use as a medicinal herb for sale in *Cannabis* dispensaries.

'Harlequin' bag seed from circa 2008-2010 was germinated and chemically analyzed for lineages with unique cannabinoid profiles. Parental germplasms were selected from this screening and a number of self and sib crosses were performed (generally referred to as F1, even though some were selfed and technically S1). Representative samples from these F1 were again germinated and screened chemically, keeping only those varieties that contained elevated levels of tetrahydrocannabivarin (THCV) compared to a non-producing control. Those meeting the criteria of producing significantly more THCV than non-producers were kept as germplasm for final evaluation. In this group, 3 classes of individual were identified: plants making less than 1% THCV, plants making between 1%-5% THCV, and plants making greater than 5% THCV. The final class fell into a group that is known as 1:1 THCV: THC producer. Seed from the final class were selected and either selfed or sib crossed. The claimed variety is one of the germplasm identified chemically from a selfed population created from seed selected from the final class. 'LPA004' was selected due to its unique properties, and was thereafter clonally propagated.

The specific steps for the breeding methodology for the creation of 'LPA004' were as follows:

1. Seeds of a commercial variety called 'Harlequin' (unpatented) were chemically screened for the production of THCVA. Through such chemical screening, a single male plant was found that produced THCVA.

2. Plants from seeds thus screened were crossed to create a first sib-cross population by crossing the male plant that was found to produce THCVA to a female sibling from the same seed population that was found in the screening process to not make THCVA. The first sib-cross population was created in this way because only the male was found to make THCVA, as determined by leaf potency testing. The male plant that became the donor parent for the line produced about 1.2% THCVA in the leaf.

3. The resulting seed population (F1) was then screened again for the production of THCVA. From the resultant seed population (sib cross donor male to non-THCV-producing female), offspring were again screened and the highest producing male and several THCVA-producing female plants were selected to generate the 2nd generation sib-cross population.

4. The seed resulting from the 2nd sib-cross were then screened for sex (only females were selected) and for THCVA production.

5. The top 4 THCVA producing females were selected and hermaphroditism was chemically induced so that each plant could produce pollen. Then each plant was subjected to a selfing round to produce feminized THCVA-producing seed (S1, but F3 generation from original 'Harlequin' seed). (Note: all subsequent descriptions of selfed females are based on this same approach.)

6. Ten seeds from each of the four selfed females were selected and germinated. All forty plants were then tested for THCVA production, and the single highest producer from each of the four independent self crosses was selected to produce a final set of THCVA-producing seed stock (S2, but F4 generation from original 'Harlequin' seed).

7. Seed was multiplied by conducting a final round of single-branch self crosses. In each plant, pollen from a single male branch was contacted with female flowers also from a single branch to produce the seed stock.

8. These four seed populations were transferred to from the breeder to the Applicant (S3, but F5 generation from 'Harlequin' seed).

9. 'LPA004' came from leaf-screening the four seed populations and selecting the highest producer (Seed lot HA-4).

10. 'LPA004' was then clonally propagated to maintain the genetic line.

Selection criteria included THCV levels.

The selection was subsequently evaluated for 2 years at Salinas, CA.

Plants of the new variety differ from plants of the seed parent 'Harlequin' primarily in being highly sensitive to overwatering, highly sensitive to photoperiod changes, and production of moderate to high levels of the minor cannabinoid THCVA. Plants are generally very late finishing (very slow flower maturation) unless light deprivation is used. Plants are also very nutrient sensitive. Unmanicured (outdoor grown) plant height can reach over 12 feet. Plants show strong anthocyanin in stems and petioles when grown indoors using UV lights. Flower tends to be less dense than parental type. Pollen production from reversed females is generally lower than expected due to the slow maturation of the flower.

BRIEF DESCRIPTION OF THE DRAWINGS

The accompanying photographic illustrations show the typical appearance of the new variety 'LPA004'. The colors are as nearly true as is reasonably possible in a color representation of this type. Colors in the photographs may differ slightly from the color values cited in the detailed botanical description, which accurately describes the colors of the new plant. The patent or application file contains at least one drawing executed in color. Copies of this patent or patent application publication with color drawing(s) will be provided by the Office upon request and payment of the necessary fee.

DETAILED DESCRIPTION

Figure 1:
FIG. 1 is a photograph of the whole plant of the new variety 'LPA004' at week 4 of flower.
Figure 2:
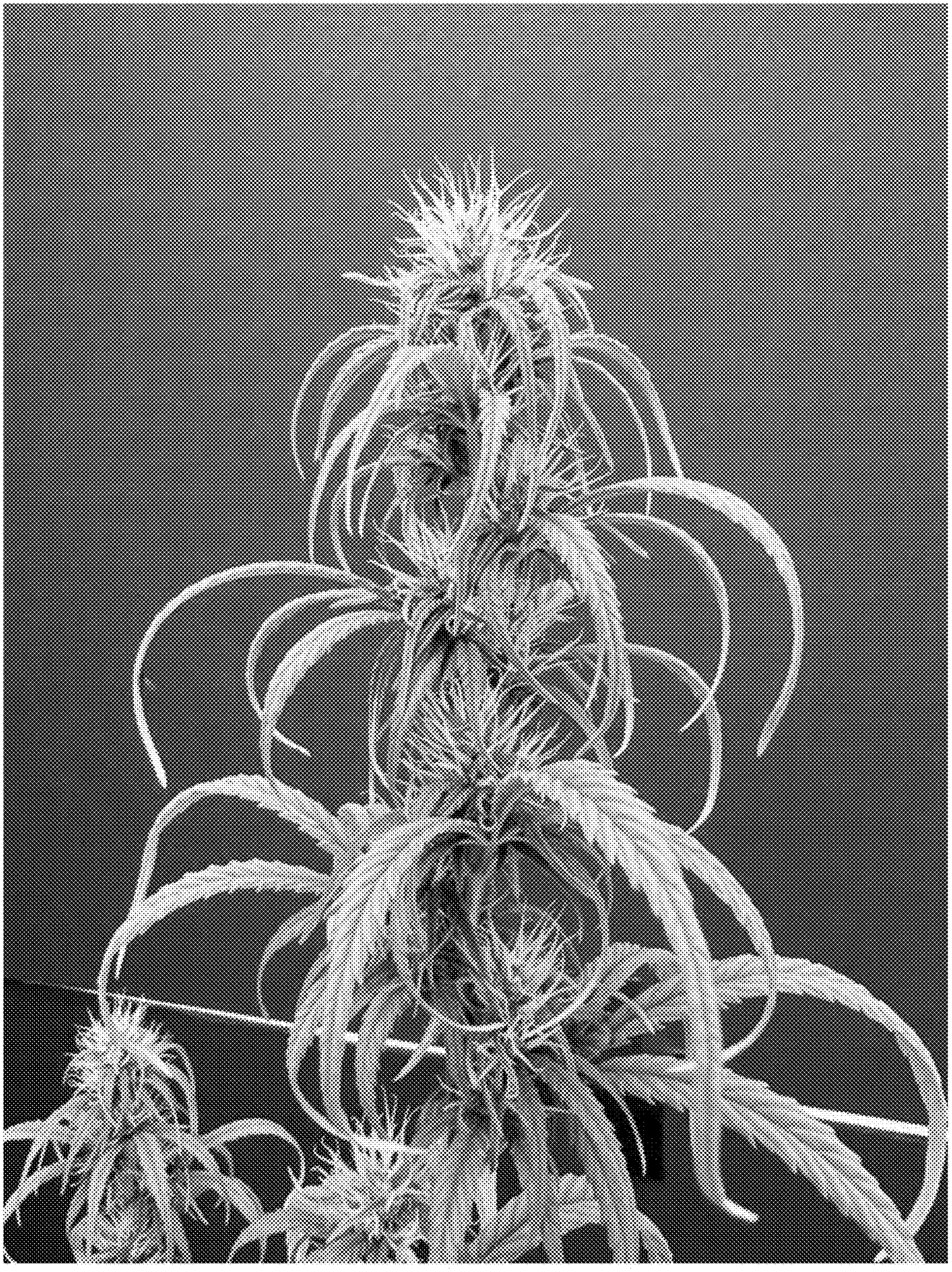
FIG. 2 is a photograph of the new variety 'LPA004' at week 4 of flower, depicting the narrowness and length of the leaves associated with the inflorescence.
Figure 3:
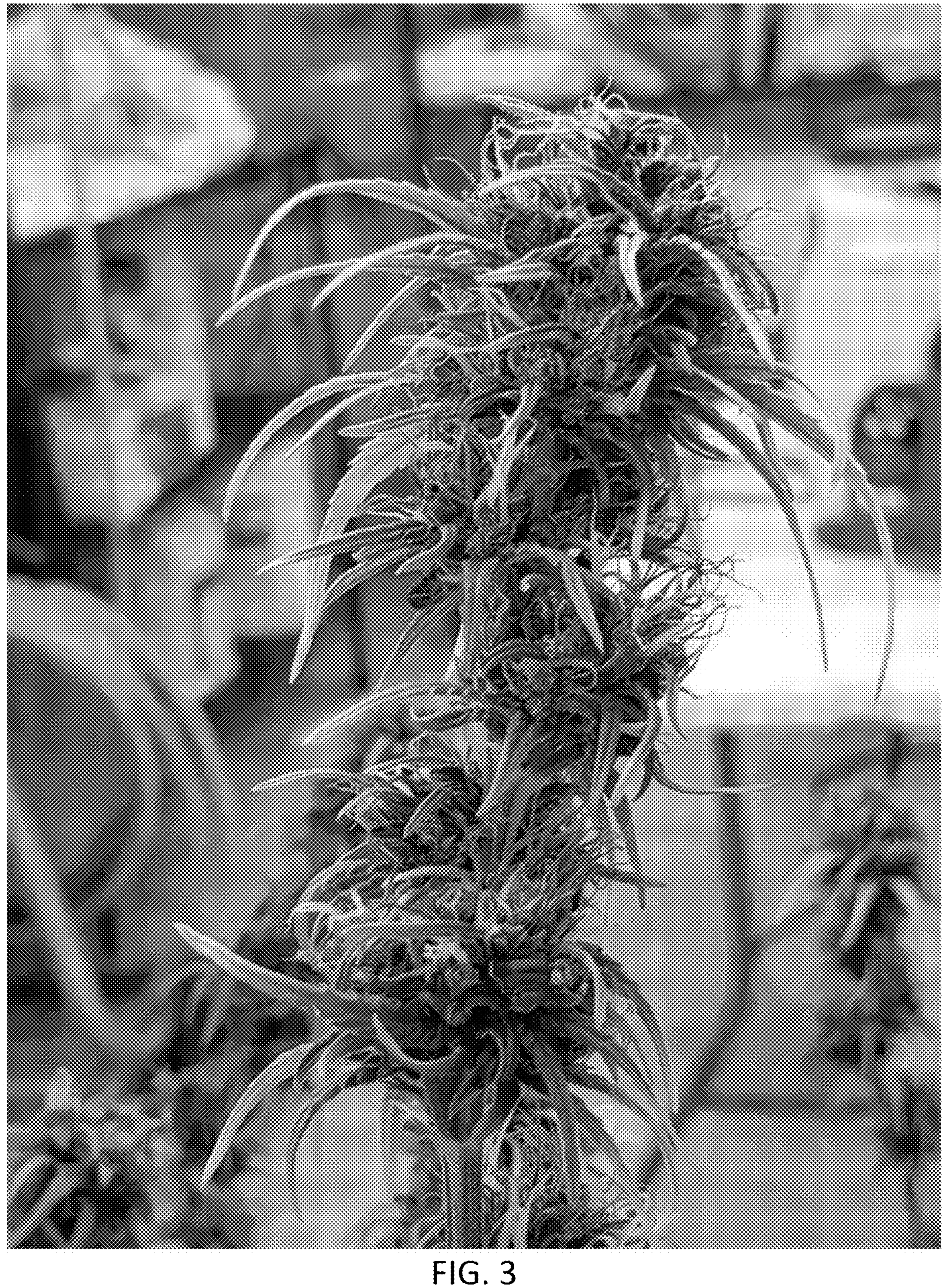
FIG. 3 is a photograph of the fully mature flower of the new variety 'LPA004' showing size and shape of the inflorescence crown, coloration at maturity, trichome deposition, and length and color of the stigma (brown is mature, white is not fully mature).
Figure 4:
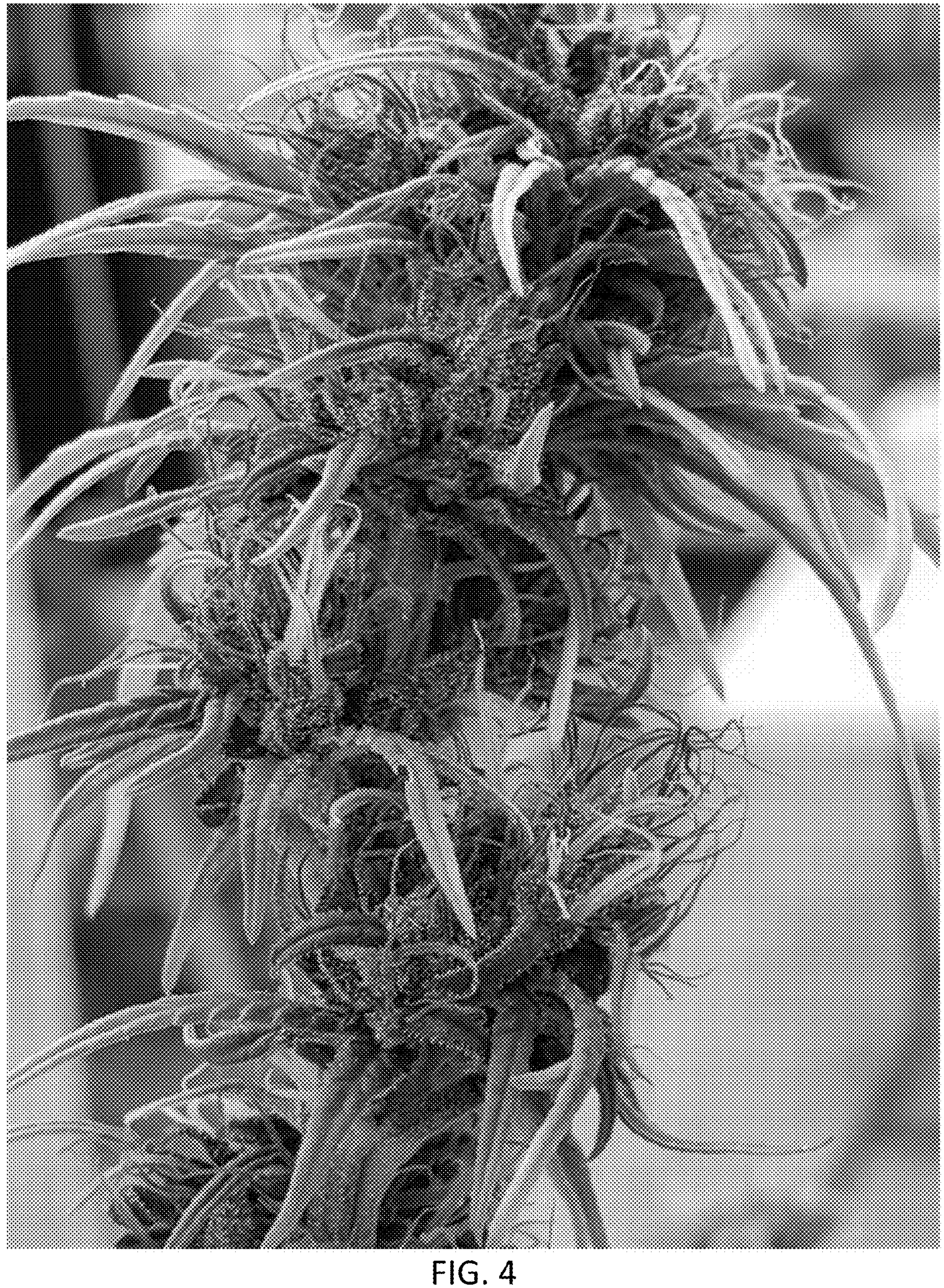
FIG. 4 is a photograph of the fully mature flower of the new variety 'LPA004' showing size and shape of inflorescence crown, coloration at maturity, trichome deposition, and length and color of the stigma.
Figure 5:
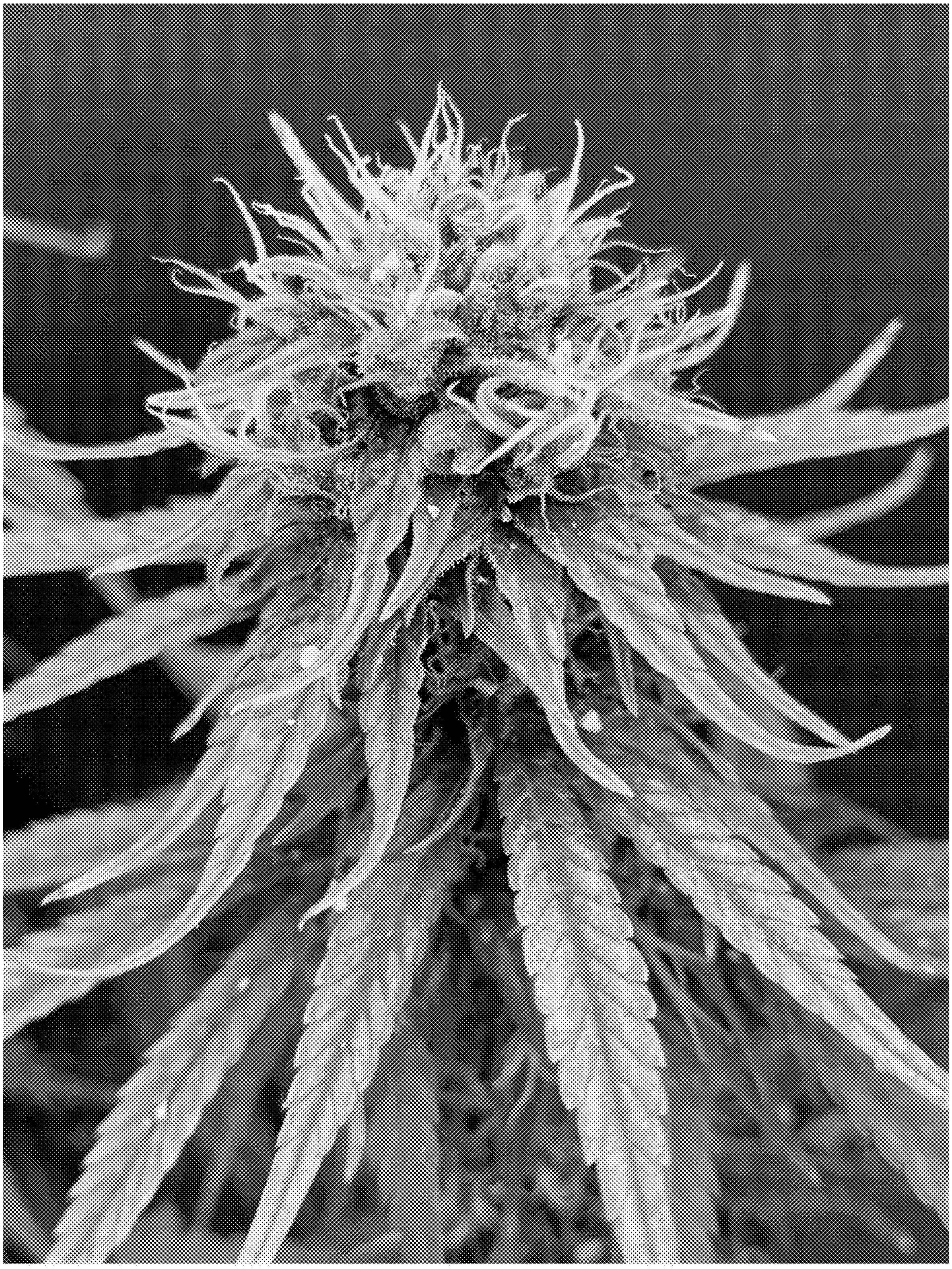
FIG. 5 is a photograph of the fully mature flower of the new variety 'LPA004' showing size and shape of inflorescence crown, coloration at maturity, trichome deposition, and length and color of the stigma.
Figure 6:
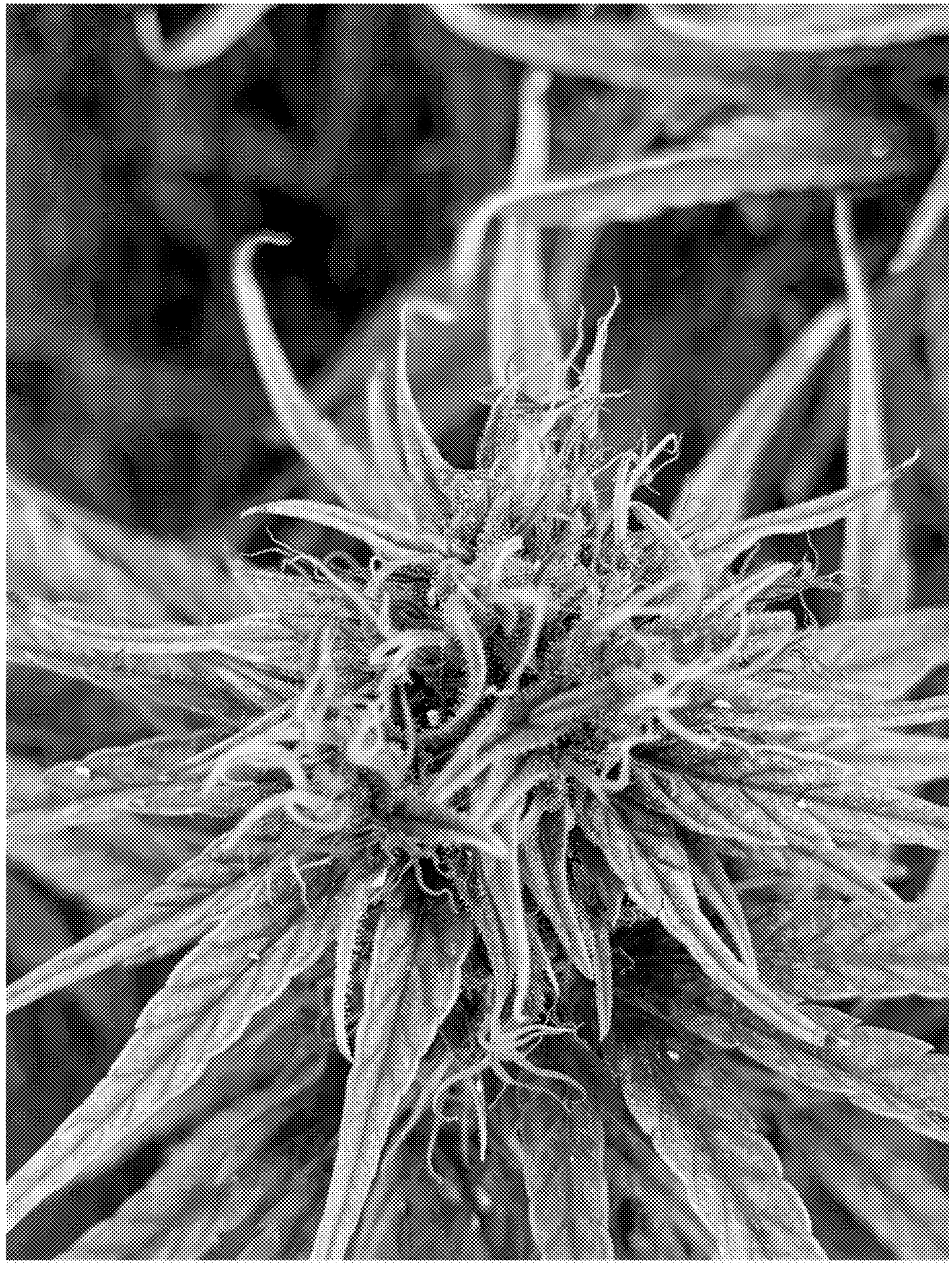
FIG. 6. is a photograph of the fully mature flower of the new variety 'LPA004' showing size and shape of inflorescence crown, coloration at maturity, trichome deposition, and length and color of the stigma.

Some embodiments of the invention relate to a seed from a *Cannabis* plant designated 'LPA004' wherein a representative sample of seed of said plant has been deposited under accession number NCIMB 44803 on Jul. 27, 2026, at National Collection of Industrial, Food and Marine Bacteria (NCIMB) Ltd. Located at Wellshead Place, Aberdeen, Dyce, AB21 7GB Scotland. Upon issuance of a patent, all restrictions imposed by the depositor on the availability to the public of the deposited material will be irrevocable removed, and the deposit is intended to meet all the requirements of 37 C.F.R. §§ 1.801-1.809. The deposity has been accepted under the Budapest Treaty and will be maintained in the depository for a period of 30 years, 5 years after the last request, or the effective life of the patent, whichever is longer, and will be replaced if necessary during that period.

Some embodiments of the invention relate to a *Cannabis* plant, or plant part, tissue, or cell thereof produced by growing the seed of 'LPA004', or a descendant thereof. Plant parts can include the embryo, shoot, root, stem, seed, stipule, leaf, petal, flower bud, flower, ovule, bract, trichome, branch, petiole, internode, bark, pubescence, tiller, rhizome, frond, blade, ovule, pollen, stamen, and the like.

The plants, or plant parts of the invention can display a cannabinoid profile within the ranges set forth herein. The productivity of any given cannabinoid and/or the amounts or ratios of cannabinoids, terpenes, and other plant products can be, by nature, quite variable. The variability can be contributed to by weather, latitude, soil and feeding conditions, pathogens, and numerous other agronomic, horticultural, and biological factors.

Some embodiments of the invention relate to methods of using the plant in a breeding program to produce *cannabis* progeny including a cannabinoid profile generally within the ranges as set forth in Table 1. Details of existing *Cannabis* plant varieties and breeding are described in Potter et al. (2011, *World Wide Weed: Global Trends in Cannabis Cultivation and Its Control*); Holland (2010, *The Pot Book: A Complete Guide to Cannabis*, Inner Traditions/Bear & Co, ISBN1594778981, 9781594 778988); Green I (2009, *The Cannabis Grow Bible: The Definitive Guide to Growing Marijuana for Recreational and Medical Use*, Green Candy Press, 2009, ISBN 1931160589, 9781931160582); Green II (2005, *The Cannabis Breeder's Bible: The Definitive Guide to Marijuana Genetics, Cannabis Botany* and *Creating* Strains *for the Seed Market*, Green Candy Press, 1931160279, 9781931160278); Starks (1990, *Marijuana Chemistry Genetics, Processing & Potency*, ISBN 0914171399, 9780914171393); Clarke (1981, *Marijuana Botany, an Advanced Study: The Propagation and Breeding of Distinctive Cannabis*, Ronin Publishing, ISBN 091417178X, 9780914171782); Short (2004, *Cultivating Exceptional Cannabis: An Expert Breeder Shares His Secrets*, ISBN 1936807122, 9781936807123); Cervantes (2004, *Marijuana Horticulture: The Indoor/Outdoor Medical Grower's Bible*, Van Patten Publishing, ISBN 187882323X, 9781878823236); Franck et al. (1990, *Marijuana Grower's Guide*, Red Eye Press, ISBN 0929349016, 9780929349015); Grotenhermen and Russo (2002, *Cannabis and Cannabinoids: Pharmacology, Toxicology, and Therapeutic Potential*, Psychology Press, ISBN 0789015080, 9780789015082); Rosenthal (2007, *The Big Book of Buds: More Marijuana Varieties from the World's Great Seed Breeders*, ISBN 1936807068, 9781936807062); Clarke, R C (*Cannabis: Evolution and Ethnobotany* 2013); King, J (*Cannabible* Vols 1-3, 2001-2006); and four volumes of Rosenthal's Big Book of Buds series (2001, 2004, 2007, and 2011), each of which is herein incorporated by reference in its entirety for all purposes.

The present invention also relates to variants, mutants, and minor modifications of the seeds, plant parts, and/or whole plants of the *Cannabis* plants of the present invention. Variants, mutants, and minor modifications of the seeds, plants, plant parts, plant cells of the present invention can be generated by methods well known and available to one skilled in the art, including but not limited to, mutagenesis (e.g., chemical mutagenesis, radiation mutagenesis, transposon mutagenesis, insertional mutagenesis, signature tagged mutagenesis, site-directed mutagenesis, and natural mutagenesis), knock-outs/knock-ins, antisense, and RNA interference. For more information about mutagenesis in plants, such as agents and protocols, see Acquaah et al. (*Principles of plant genetics and breeding*, Wiley-Blackwell, 2007, ISBN 1405136464, 9781405136464) which is herein incorporated by reference in its entirety. Other kinds of modifications practiced in the *Cannabis* industry, including but not limited to feminization of seeds and/or day-length neutrality/autoflowering are also within the scope of the invention and are within the level of skill in the art to execute.

The present invention also relates to a mutagenized population of the *Cannabis* plants of the present invention, and methods of using such populations. In some embodiments, the mutagenized population can be used in screening for new *Cannabis* lines which comprises one or more or all of the morphological, physiological, biological, and/or chemical characteristics of *Cannabis* plants of the present invention.

In some embodiments, the new *Cannabis* plants obtained from the screening process comprise one or more or all of the morphological, physiological, biological, and/or chemical characteristics of *Cannabis* plants of the present invention, and one or more additional or different or new morphological, physiological, biological, and/or chemical characteristic.

The present invention also provides any compositions or any products made from or isolated from the plants of the present invention. In some embodiments, the compositions/products comprise an extract of the plants. In some embodiments, the extract can contain a higher percentage of terpenes/terpenoids compared to the extract isolated from a control *Cannabis* plant variety (e.g., an existing variety, such as a recreational *Cannabis* plant variety). In some embodiments, the invention relates to a smokable or edible product comprising the *Cannabis* plant, or plant part, tissue, cell, extract, or isolate.

The present invention provides methods of using the *Cannabis* plants or any plant parts, any compositions, or any chemicals derived from said plants of the present invention.

In some embodiments, the plants of the present invention can be used to produce new plant varieties. In some embodiments, the plants are used to develop new varieties or hybrids with desired phenotypes or genotypes.

In some embodiments, selection methods (e.g., molecular marker assisted selection) can be combined with breeding methods to accelerate the selection process. Additional breeding methods known to those of ordinary skill in the art include, e.g., methods discussed in Chahal and Gosal (*Principles and procedures of plant breeding: biotechnological and conventional approaches*, CRC Press, 2002, ISBN 084931321X, 9780849313219); Taji et al. (*In vitro plant breeding*, Routledge, 2002, ISBN 156022908X, 9781560229087); Richards (*Plant breeding systems*, Taylor & Francis US, 1997, ISBN 0412574500, 9780412574504); Hayes (*Methods of Plant Breeding*, Publisher: READ BOOKS, 2007, ISBN1406737062, 9781406737066); each of which is incorporated by reference in its entirety. The *Cannabis* genome has been sequenced (Bakel et al., The draft genome and transcriptome of *Cannabis sativa, Genome Biology,* 12(10):R102, 2011). Molecular makers for *Cannabis* plants are described in Datwyler et al. (Genetic variation in hemp and marijuana (*Cannabis sativa* L.) according to amplified fragment length polymorphisms, *J Forensic Sci.* 2006 March; 51(2):371-5.); Pinarkara et al., (RAPD analysis of seized marijuana (*Cannabis sativa* L.) in Turkey, *Electronic Journal of Biotechnology,* 12(1), 2009), Hakki et al., (Inter simple sequence repeats separate efficiently hemp from marijuana (*Cannabis sativa* L.), *Electronic Journal of Biotechnology,* 10(4), 2007); Gilmore et al. (Isolation of microsatellite markers in *Cannabis sativa* L. (marijuana), *Molecular Ecology Notes,* 3(1): 105-107, March 2003); Pacifico et al., (Genetics and marker assisted selection of chemotype in *Cannabis sativa* L.), *Molecular Breeding* (2006) 17:257-268); and Mendoza et al., (Genetic individualization of *Cannabis sativa* by a short tandem repeat multiplex system, *Anal Bioanal Chem* (2009) 393: 719-726); each of which is herein incorporated by reference in its entirety.

In some embodiments, the *Cannabis* plant, or plant part, tissue, or cell of 'LPA004' comprises a cannabinoid profile and a terpene profile as set forth herein In some embodiments, the invention relates to a *Cannabis* clone regenerated from the *Cannabis* plant or descended from the plant, or plant part, tissue, cell, or seed of 'LPA004' wherein the plant is a clonal descendent.

In some embodiments, the invention relates to a method of producing an F1 *Cannabis* seed, wherein the method includes crossing the plant with a different *Cannabis* plant and harvesting the resultant F1 *Cannabis* seed. In some embodiments, the invention relates to the F1 hybrid *Cannabis* seed produced by this method. In some embodiments, the invention relates to a F1 hybrid *Cannabis* plant produced by growing the F1 hybrid *Cannabis* seed. In some embodiments, the invention relates to a *Cannabis* clone regenerated from the F1 hybrid *Cannabis* plant. In some embodiments, the invention relates to a smokable or edible product comprising *Cannabis* tissue from the F1 hybrid *Cannabis* plant.

In some embodiments the invention relates to seed line from a clonally propagated plant of the new variety. In some embodiments, the seed line is that of the deposited seed recited herein. In other embodiments, the seed line is one that is separately established through inbreeding and selection of plants of the new variety, using pollen from reversed females of the new variety and/or from relatives/ancestors of the new variety. In these embodiments, crosses and selections are conducted through successive generations to obtain a line of seed that stably produces progeny having physical and chemical properties within the ranges recited herein for the new variety. In some embodiments, this seed line is feminized seed, having been feminized using techniques known to those of skill in the art.

Tables 1 and 2 provide exemplary profiles of key cannabinoids and terpenes, respectively. Each column of each table is provided as an example. The data for Example 3 are provided from laboratory tests of cannabinoids from a sample of dried flower of 'LPA004'. The data for Examples 1, 2, 4, and 5 are provided to demonstrate possible ranges of variation in cannabinoid accumulation in dried flower, taking into account the variability that is known to exist in numerous cultivars of *Cannabis* when cultivated under different conditions. Likewise, the data for Example 8 are provided from laboratory test of terpenes from a sample of dried flower of 'LPA004.' The data for Examples 6, 7, 9, and 10 are provided to demonstrate possible ranges of variation in terpene accumulation in dried flower, taking into account the variability that is known to exist in numerous cultivars of *Cannabis* when cultivated under different conditions. The following detailed description sets forth the distinctive characteristics of 'LPA004'.

TABLE 1

Exemplary Profiles of Key Cannabinoids.

| | Ex 1 Percent | Ex 2 Percent | Ex 3 Percent | Ex 4 Percent | Ex 5 Percent |
|---|---|---|---|---|---|
| Total Cannabinoids | 0.8540% | 4.2700% | 12.9502% | 24.2000% | 29.0400% |
| Total THC | 0.2118% | 1.0590% | 5.4410% | 10.1800% | 12.2160% |
| Total CBD | 0.0000% | 0.3818% | 0.7635% | 4.2000% | 5.0400% |
| THCA | 0.2416% | 1.2080% | 6.0890% | 11.5030% | 13.8036% |
| THCVA | 0.6438% | 3.2190% | 7.1313% | 11.7860% | 14.1432% |
| CBGA | 0.0120% | 0.0600% | 0.6693% | 1.2260% | 1.4712% |
| delta9THC | 0.0000% | 0.0502% | 0.1003% | 0.2900% | 0.3480% |
| THCV | 0.0154% | 0.0770% | 0.4328% | 1.9240% | 2.3088% |
| CBG | 0.0000% | 0.0281% | 0.0562% | 0.1270% | 0.1524% |
| CBCA | 0.0100% | 0.0500% | 0.0755% | 0.1200% | 0.1440% |
| CBDA | 0.0000% | 0.0126% | 0.0252% | 0.0600% | 0.0720% |

*Total THC = Δ9THC + (THCa * 0.877)

**Total CBD = CBD + (CBDa * 0.877)

***Total Cannabinoids = Total THC + Total CBD + Total CBG + Total THCV + Total CBC + Total CBDV + Δ8THC + CBL + CBN

TABLE 2

Exemplary Profiles of Key Terpenes.

| | Ex 6 Percent | Ex 7 Percent | Ex 8 Percent | Ex 9 Percent | Ex 10 Percent |
|---|---|---|---|---|---|
| Myrcene | 0.0019% | 0.0096% | 0.2357% | 0.7200% | 0.8640% |
| Beta Caryophyllene | 0.0000% | 0.1239% | 0.2477% | 0.4764% | 0.5717% |
| Ocimene | 0.0000% | 0.0831% | 0.1662% | 0.3700% | 0.4440% |
| Limonene | 0.0000% | 0.0481% | 0.0962% | 0.2270% | 0.2724% |
| Alpha Pinene | 0.0000% | 0.0786% | 0.1571% | 0.2463% | 0.2956% |
| Alpha Humulene | 0.0000% | 0.0533% | 0.1067% | 0.2063% | 0.2476% |
| Beta Pinene | 0.0000% | 0.0270% | 0.0539% | 0.0800% | 0.0960% |
| Linalool | 0.0008% | 0.0038% | 0.0151% | 0.0300% | 0.0360% |
| Fenchol | 0.0006% | 0.0030% | 0.0155% | 0.0300% | 0.0360% |
| Nerolidol | 0.0006% | 0.0029% | 0.0152% | 0.0284% | 0.0341% |
| Guaiol | 0.0014% | 0.0072% | 0.0176% | 0.0289% | 0.0347% |
| Terpineol | 0.0000% | 0.0054% | 0.0108% | 0.0200% | 0.0240% |
| Caryophyllene Oxide | 0.0014% | 0.0070% | 0.0223% | 0.0416% | 0.0499% |
| Borneol | 0.0000% | 0.0019% | 0.0038% | 0.0077% | 0.0092% |
| Camphene | 0.0000% | 0.0019% | 0.0037% | 0.0063% | 0.0076% |
| R-(+)-Pulegone | 0.0000% | 0.0026% | 0.0052% | 0.0261% | 0.0313% |
| Alpha Bisabolol | 0.0000% | 0.0060% | 0.0121% | 0.0247% | 0.0296% |
| Camphor | 0.0000% | 0.0002% | 0.0003% | 0.0016% | 0.0019% |
| Terpene Total | 0.0219% | 0.1094% | 1.4263% | 2.7924% | 3.3509% |

Detailed Botanical Description

The following detailed description sets forth the distinctive characteristics of 'LPA004'. The data which defines these characteristics was collected from asexual reproductions of the original selection. Dimensions, sizes, colors, averages, and other characteristics are approximations and set forth as accurately as possible. The descriptions relate to plants grown in Salinas, CA. Color notations are in reference to the Royal Horticultural Society Colour Chart. Variations in colors are indicated by providing numerous color codes for a given descriptive.

Type: Herbaceous tap-rooted annual

Classification:

a. Family—Cannabaceae.

b. Genus—*Cannabis*.

c. Species—*sativa*.

d. Common Name—Marijuana.

Plant

General:

a. Parentage:

i. Male parent—unknown, posited to be African landrace.

ii. Female parent—'Harlequin' (not patented).

b. Growth rate—Growth rate is slower when plant is younger and establishing itself in soil. Once it is established and flipped to flower cycle, growth rate is average to faster than average in height.
c. Fragrance—Subtle, herbaceous, grassy.
d. Proportion of hermaphrodite plants—Low.
e. Type of inflorescence—Branched compound raceme.
f. Photoperiodicity—Vegetative: 18/6; Flower: 12/12.
g. Pollen description—Light yellow, low producer.

Stem

General:
a. Shape—Round.
b. Depth of grooves—Shallow.
c. Pith in cross section—Thin.
d. Color—138D/N144C.

Leaf

General:
a. Leaf color (Top side)—143A/139B.
b. Leaf color (Under side)—146B/146C.
c. Leaf arrangement—Primarily Alternate.
d. Leaf shape—Palmate compound.
e. Leaf margins—Strong serration with teeth pointing towards apex of leaflet.
f. Leaf apex shape—Acuminate.
g. Leaf base shape—Cuneate.
h. Average leaf length—14 cm.
i. Number of leaflets per leaf—3-7.
j. Central leaflet length—Long.
k. Central leaflet width—Narrow.
l. Margin type—Serrate.
m. Trichome type (top surface)—Capitate *sessile*.
n. Trichome type (bottom surface)—Capitate *sessile*.
o. Texture of top and bottom surfaces-Top: rough; bottom: pubescent.
p. Venation type—Pinnate.

Petiole

General:
a. Length—Medium.
b. Surface texture—Pubescent.
c. Anthocyanin intensity—Medium/strong.
d. Color—Upper: N92A; lower: N97A/B.

Female Flower

General:
a. Description when flower has styles on the first flowers—Styles are white and wispy. These first flowers create a dome over the tops of each branch as there are many pistils present.
b. General description of pistil—Pistils are long and white before they are ready to harvest. When ready to harvest, they darken from white to a light warm brown but remain long and wispy. The pistil consists of one ovary but two carpels.
c. General description of cola—Colas are thin and sparse, not dense.
d. General description of node—Nodes in finished flower are close together in colas. They grow in length as you move down the stem.
e. Bract
  i. Size—Average of 4.75 mm.
  ii. Shape—Apex is pointed. Base is small shoulder.
  iii. Trichome type—Cystolithic hairs and capitate-stalked.
f. Stigma
  i. Quantity—2 per ovary.
  ii. Trichome type—Capitate *sessile* with moderate density.
  iii. Color—8D/N167B or N167C.

A seed sample of this invention, will be deposited prior to issuance with as established under the Budapest Treaty according to 37 CFR 1.803(a)(1). To satisfy the enablement requirements of 35 U.S.C. 112, and to certify that the deposit of the *Cannabis* Plant Named LPA004 of the present invention meets the criteria set forth in 37 CFR 1.801-1.809 and Manual of Patent Examining Procedure (MPEP) 2402-2411.05, Applicant(s) hereby makes the following statements regarding the deposited *Cannabis* Plant Named LPA004: If the deposit is made under the terms of the Budapest Treaty, the instant invention will be irrevocably and without restriction released to the public upon the granting of a patent. If the deposit is made not under the terms of the Budapest Treaty, Applicant(s) provides assurance of compliance by the following statements: 1. During the pendency of this application, access to the invention will be afforded to the Commissioner upon request; 2. All restrictions on availability to the public will be irrevocably removed upon granting of the patent under conditions specified in 37 CFR 1.808; 3. The deposit will be maintained in a public repository for a period of 30 years or 5 years after the last request or for the effective life of the patent, whichever is longer; 4. A test of the viability of the biological material at the time of deposit will be conducted by the public depository under 37 CFR 1.807; and 5. The deposit will be replaced if it should ever become unavailable. Access to this deposit will be available during the pendency of this application to persons determined by the Commissioner of Patents and Trademarks to be entitled thereto under 37 C.F.R. § 1.14 and 35 U.S.C. § 122. Upon granting of any claims in this application, all restrictions on the availability to the public of the variety will be irrevocably and without restriction or condition removed by affording access to a deposit of the seed sample of the same *Cannabis* plant designated 'LPA004' with the depository

What is claimed is:

1. A seed from *Cannabis* plant designated 'LPA004' wherein a representative sample of seed of said plant has been deposited under accession number NCIMB 44803.

2. A *Cannabis* plant, or plant part, tissue, or cell thereof produced by growing the seed of claim 1.

3. The *Cannabis* plant, or plant part, tissue, or cell thereof of claim 2, wherein a flower produced from said *Cannabis* plant or plant part, tissue, or cell thereof comprises a cannabinoid profile of:
(a) THCA between 0.2416% and 13.8036%;
(b) THCVA between 0.6438% and 14.1432%;
(c) CBGA between 0.0120% and 1.4712%;
(d) delta9THC between 0.0000% and 0.3480%;
(e) THCV between 0.0154% and 2.3088%;
(f) CBG between 0.0000% and 0.1524%;
(g) CBCA between 0.0100% and 0.1440%;
(h) CBDA between 0.0000% and 0.0720%;
(i) Total THC between 0.2118% and 12.2160%;
(j) Total CBD between 0.0000% and 5.0400%; and
(k) Total Cannabinoids between 0.8540% and 29.0400%,
and a terpene profile of:
(a) Myrcene between 0.0019% and 0.8640%;
(b) Beta Caryophyllene between 0.0000% and 0.5717%;
(c) Ocimene between 0.0000% and 0.4440%;
(d) Limonene between 0.0000% and 0.2724%;
(e) Alpha Pinene between 0.0000% and 0.2956%;
(f) Alpha Humulene between 0.0000% and 0.2476%;
(g) Beta Pinene between 0.0000% and 0.0960%;
(h) Linalool between 0.0008% and 0.0360%;
(i) Fenchol between 0.0006% and 0.0360%;
(i) Nerolidol between 0.0006% and 0.0341%
(k) Guaiol between 0.0014% and 0.0347%;
(l) Terpineol between 0.0000% and 0.0240%;

(m) Caryophyllene Oxide between 0.0014% and 0.0499%;
(n) Borneol between 0.0000% and 0.0092%;
(o) Camphene between 0.0000% and 0.0076%;
(p) R-(+)-Pulegone between 0.0000% and 0.0313%;
(q) Alpha Bisabolol between 0.0000% and 0.0296%
(r) Camphor between 0.0000% and 0.0019%; and(s)
(s) Total Terpene between 0.0219% and 3.3509%,
and wherein the percent-value is weight % by dry weight of said flower.

4. A method of breeding a *Cannabis* plant, comprising crossing the *Cannabis* plant of claim 2 with itself or a second *Cannabis* plant to produce *Cannabis* seed and *Cannabis* progeny plant thereof, wherein a flower produced from said *Cannabis* progeny plant comprises a cannabinoid profile-of:
(a) THCA between 0.2416% and 13.8036%;
(b) THCVA between 0.6438% and 14.1432%;
(c) CBGA between 0.0120% and 1.4712%;
(d) delta9THC between 0.0000% and 0.3480%;
(e) THCV between 0.0154% and 2.3088%;
(f) CBG between 0.0000% and 0.1524%;
(g) CBCA between 0.0100% and 0.1440%;
(h) CBDA between 0.0000% and 0.0720%;
(i) Total THC between 0.2118% and 12.2160%;
(i) Total CBD between 0.0000% and 5.0400%;
(k) Total Cannabinoids between 0.8540% and 29.0400%, and a terpene profile of:
(a) Myrcene between 0.0019% and 0.8640%;
(b) Beta Caryophyllene between 0.0000% and 0.5717%;
(c) Ocimene between 0.0000% and 0.4440%;
(d) Limonene between 0.0000% and 0.2724%;
(e) Alpha Pinene between 0.0000% and 0.2956%;
(f) Alpha Humulene between 0.0000% and 0.2476%;
(g) Beta Pinene between 0.0000% and 0.0960%;
(h) Linalool between 0.0008% and 0.0360%;
(i) Fenchol between 0.0006% between 0.0360%;
(j) Nerolidol between 0.0006% and 0.0341%;
(k) Guaiol between 0.0014% between 0.0347%;
(l) Terpineol between 0.0000% between 0.0240%;
(m) Caryophyllene Oxide between 0.0014% and 0.0499%;
(n) Borneol between 0.0000% and 0.0092%;
(o) Camphene between 0.0000% and 0.0076%;
(p) R-(+)-Pulegone between 0.0000% and 0.0313%;
(g) Alpha Bisabolol between 0.0000 and 0.0296%
(r) Camphor between 0.0000% and 0.0019%; and
(s) Total Terpene between 0.0219% and 3.3509%,
and wherein the percent-value is weight % by dry weight of said flower.

5. The *Cannabis* plant part of claim 2, wherein said plant part is selected from the group consisting of: stems, trichomes, leaves, and flower buds.

6. A *Cannabis* plant produced by the *Cannabis* plant of claim 2, wherein the production is by clonal propagation.

* * * * *